United States Patent
Karmali

(10) Patent No.: US 7,378,054 B2
(45) Date of Patent: May 27, 2008

(54) SPECIMEN COLLECTING, PROCESSING AND ANALYTICAL ASSEMBLY

(75) Inventor: Rashida A. Karmali, New York, NY (US)

(73) Assignee: Savvipharm Inc, New York, NY (US)

( * ) Notice: Subject to any disclaimer, the term of this patent is extended or adjusted under 35 U.S.C. 154(b) by 193 days.

(21) Appl. No.: 10/826,083

(22) Filed: Apr. 16, 2004

(65) Prior Publication Data

US 2005/0232813 A1    Oct. 20, 2005

(51) Int. Cl.
*B01L 3/00* (2006.01)

(52) U.S. Cl. .......................... 422/57; 422/58; 422/61; 422/99; 422/102

(58) Field of Classification Search ................ 422/57, 422/58, 61, 99, 102; 436/69, 70, 174, 175, 436/176, 179, 180

See application file for complete search history.

(56) References Cited

U.S. PATENT DOCUMENTS

| | | | |
|---|---|---|---|
| 3,951,606 A * | 4/1976 | Moyer et al. ................. | 422/73 |
| 4,214,874 A * | 7/1980 | White .................... | 73/864.01 |
| 4,235,601 A | 11/1980 | Deutsch et al. | |
| 4,248,973 A | 2/1981 | Kallis | |
| 4,299,916 A | 11/1981 | Litman et al. | |
| 4,409,988 A | 10/1983 | Greenspan | |
| 4,418,702 A | 12/1983 | Brown et al. | |
| 4,447,546 A | 5/1984 | Hirschfeld | |
| 4,580,577 A | 4/1986 | O'Brien et al. | |
| 4,582,809 A | 4/1986 | Block | |
| 4,624,929 A | 11/1986 | Ullman | |
| 4,635,488 A | 1/1987 | Kremer | |
| 4,774,962 A | 10/1988 | Hebel et al. | |
| 4,820,399 A | 4/1989 | Senda et al. | |
| 4,900,663 A | 2/1990 | Wie et al. | |
| 4,978,504 A | 12/1990 | Nason | |
| 4,999,285 A | 3/1991 | Stiso | |
| 5,030,558 A | 7/1991 | Litman et al. | |
| 5,039,607 A | 8/1991 | Shold | |
| 5,056,521 A | 10/1991 | Parsons et al. | |
| 5,141,850 A | 8/1992 | Cole et al. | |
| 5,257,984 A * | 11/1993 | Kelley ........................ | 604/403 |
| 5,387,526 A * | 2/1995 | Garner et al. ............... | 436/169 |

(Continued)

FOREIGN PATENT DOCUMENTS

EP    0103426    3/1984

(Continued)

*Primary Examiner*—Jill Warden
(74) *Attorney, Agent, or Firm*—Rashida A Karmali

(57) ABSTRACT

A specimen collecting, processing and analytical assembly, designed for testing small volumes of body fluids, substances and secretions, said assembly comprising a one piece barrel assembly with a volumetrically graduated capillary tube having an open end, and optionally coated internally with an anticoagulant, a stabilizer or a preservative. The barrel assembly includes a filter membrane fitted above the capillary end at the junction of the barrel assembly and the capillary tube, a support means at the barrel's second open end, and an analytical testing means disposed there between. The invention also provides a sealed vial containing an analytical testing reagent, the vial being substantially airtight and sealed with a pierceable material, a first tip cap for closing the open end of the capillary tube, a second cap to close sealably the second open end of the barrel container and a lancet to induce capillary skin punctures.

11 Claims, 3 Drawing Sheets

U.S. PATENT DOCUMENTS

| | | | |
|---|---|---|---|
| 5,556,598 A * | 9/1996 | Raybuck et al. | 422/100 |
| 5,611,995 A | 3/1997 | de Zoeten et al. | |
| 5,622,871 A | 4/1997 | May et al. | |
| 5,656,502 A | 8/1997 | MacKay et al. | |
| 5,731,512 A * | 3/1998 | Lewy et al. | 73/61.65 |
| 5,741,639 A * | 4/1998 | Ensing et al. | 435/6 |
| 5,766,933 A * | 6/1998 | El Shami et al. | 435/287.2 |
| 5,935,864 A | 8/1999 | Schramm et al. | |
| 5,942,407 A * | 8/1999 | Liotta et al. | 435/28 |
| 5,976,896 A * | 11/1999 | Kumar et al. | 436/527 |
| 6,117,394 A * | 9/2000 | Smith | 422/100 |
| 6,634,243 B1 | 10/2003 | Wickstead | |
| 6,869,405 B2 * | 3/2005 | Marsden | 600/573 |

FOREIGN PATENT DOCUMENTS

| | | |
|---|---|---|
| EP | 0187167 | 7/1986 |
| EP | 0354704 | 7/1989 |
| EP | 1012560 | 6/2000 |
| EP | 1012560 B1 | 6/2000 |
| GB | 2206409 | 1/1989 |
| WO | WO8808534 | 11/1988 |
| WO | WO9014163 | 11/1990 |
| WO | WO9113355 | 9/1991 |
| WO | WO 9309431 | 5/1993 |
| WO | WO9511621 | 5/1995 |

* cited by examiner

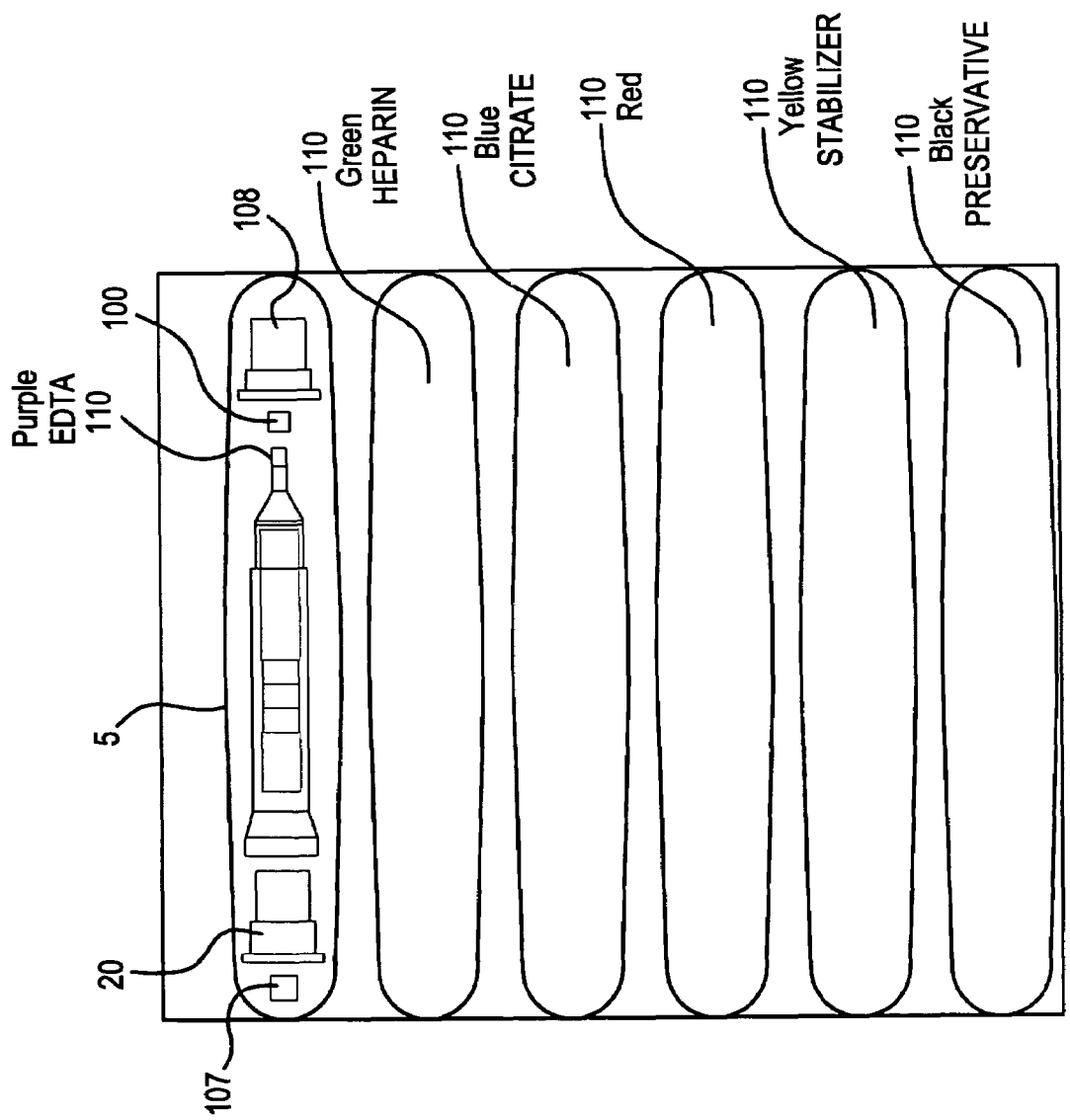

SPECIMEN COLLECTING, PROCESSING AND ANALYTICAL ASSEMBLY

1. FIELD OF INVENTION

This invention relates to sampling, processing and analytical assemblies for testing small volumes of body fluids, substances and secretions such as blood and blood products, urine, sweat, tears, pericardial fluid, peritoneal fluid, pleural fluid, cerebrospinal fluid, gastric fluid, respiratory secretions, semen, synovial fluid, vomitus, wound and ulcer drainage, ascites, amniotic fluid or saliva, for subsequent analysis, and to methods of using the assemblies in preparing and processing specimens for analysis and measurement of specific markers including, but not limited to, pathogens, pathogen products, biologics, hormones, physiological components, biochemical tests, clinical tests, diagnostic tests, drugs, or drug metabolites.

2. BACKGROUND TO THE INVENTION

There has been a growing interest in recent years in the non-intrusive clinical sampling of body fluids for detecting various chemical and biological substances. This is largely the result of improved analytical techniques and the realization that many of the components of physiological and/or pathological interest (pathogens, biologics, metabolites, drugs, etc.) contained in blood and blood product specimens obtained by intrusive means (e.g., venepuncture) are also contained in other body substances, secretions or fluids such as urine, sweat, tears, respiratory secretions, semen, vomitus, wound and ulcer drainage, or saliva, which can be obtained more easily and at reduced risk. Moreover, even when blood and blood products are used, the amounts of blood required to measure the levels of different components of interest are relatively small compared to the amounts drawn from different people.

In addition, saliva and urine samples may be advantageous for testing of some components of physiological interest. This may be illustrated by comparing the utility of urine and saliva samples to establish recent marijuana usage. Since marijuana can be detected in urine for up to 40 days after the last use of the drugs, while saliva will only show evidence of such usage within the last 48 hours, saliva samples are much more useful than urine samples for detecting recent use of the drug.

Body fluid sampling and testing typically involves four steps: 1) sample Collection 2) extraction of sample from the collection media 3) reaction of the sample with analytical reagents, and 4) detection and/or measurement of physiological or pathological active contents.

In the past, non-intrusive collection of body fluid samples has commonly been accomplished by the use of devices such as cotton swabs, absorbent papers and pads, which are used to absorb fluid samples. Once collected, these devices are placed in a vessel in which the sample is extracted into a suitable solvent by means of diffusion, with or without mechanical agitation. Sample extraction by means of unassisted diffusion is quite slow, usually requiring several minutes. If this process is sped up with agitation, extraneous material such as cotton or paper fibers may be entrained into the extraction fluid along with the sample and may have to be removed prior to the reagent reaction of step 3 above.

Chemical and biochemical analysis of liquids has been traditionally performed in specialized laboratories. The classical methods of analytical chemistry have been increasingly replaced by automated analysis designed for the processing of well-defined specimens. These procedures are typically still conducted in highly specialized institutions by technicians trained in operating particular integrated instruments.

The specimens collected and sent to these specialized clinical testing laboratories for medical diagnosis generally include specimens collected into tubes, vials or containers that hold anywhere from 5 ml to about 20 ml of the liquid sample. Specific amounts, which typically involve only a fraction of the volume collected are used directly or after centrifugation for the measurement of the test ordered. The rest of the specimen is discarded as a biohazard material.

An object of the present invention is to provide a plurality of assemblies for collecting liquid specimens in volumes sufficient to carry out triplicate tests of a specimen and to avoid collection of liquid specimens in excessive amounts, the majority of which is ultimately discarded. Specifically, the basic unit is a one piece barrel container comprising a variety of assemblies of the present invention that are designed to collect liquid specimens for analysis by using open capillary tubes to collect liquid specimens. The basic unit may further include a processing component involving dilution and filteration of the collected sample, and optionally provide an analytical means to analyze and carry out a specific test.

Blood collection for routine clinical testing is generally carried out by venepuncture and varying amounts of blood ranging from 5 ml to 20 ml are collected in vaccutainer tubes having color-coded stoppers. Any disruption of vascular endothelium such as venepuncture during blood collection is a potent stimulus to clot formation. The normal endothelial cell lining of the vessel wall plays an essential role in preventing thrombus formation. The endothelial cells are active metabolically in control of the blood flow, platelet aggregation and the coagulation cascade. Disruption of the endothelial cell surface results in unopposed smooth muscle contraction and vessel spasm. This sets the stage for thrombus formation and makes it difficult to draw blood by venepuncture. In some patients on chemotherapy, drawing blood by venepuncture is virtually impossible; and it makes it difficult to monitor drug levels.

A number of analytic procedures and devices are commonly used to test body fluids for the presence of substances of diagnostic value. Blood and urine are the body fluids most frequently tested. An advantage of blood as a test fluid is that analytes are often at relatively high concentrations and measurement of these concentrations can provide information about a patient's health.

Urine is useful for diagnostic testing when the blood component of interest (e.g., a drug or hormone) is concentrated during urine formation. However, the urine concentration of an analyte does not usually reflect the physiologically active amount of the analyte in the blood.

Not commonly used, but numerous studies have demonstrated that saliva and other types of oral fluid can provide a reliable sample for diagnostic testing involving antibodies or antigens specific for various human or animal pathogens. Oral fluids have also been shown to be useful in measuring the body levels of naturally occurring hormones or therapeutic and other drugs. A trained phlebotomist is not required as is the case with blood, nor are special arrangements for privacy-in-collection and custody of the sample required, as is the case with urine. Collection of an oral fluid sample obviates the hazard of handling blood-contaminated needles and tubes.

Virtually all samples for analysis of blood cells of their constituents such as hemoglobin, are collected into tubes containing potassium or sodium salts of elhylenediamine tetra acetic acid (EDTA). EDTA, an avid calcium chelator, serves as an effective anti-coagulant that inhibits activation of the coagulation system and production of fibrin clots. Samples with clots are not suitable for analysis of fluid components. Heparin can be used as an anticoagulant without introducing a dilution error but unfortunately, it causes platelet and leukocyte agglutination, which interferes with accurate cell enumeration. For these reasons, citrate and heparin are not routinely used for blood sample collection.

The field of competitive protein binding assays or specific binding assays has greatly expanded, as its importance in the diagnostic field has become recognized. The ability to be able to detect a specific compound and measure the compound quantitatively has permitted the monitoring of the administration of a wide variety of drugs, the determination of an imbalance in a wide variety of hormones, the quantification of physiologically active proteins, and the diagnosis of diseases through detection of a pathogen. The different techniques have been distinguished in requiring or not requiring separation steps, the nature of the signal developed by the label, the development of the signal in a solution or on a surface and the manner of the measurement for a quantitative determination. The various biochemical and immunologic procedures are set forth in scientific literature and in U.S. Pat. Nos. 4,900,663; 4,999,285; 5,030,558; 5,039,607; and 5,935,864.

U.S. Pat. No. 5,935,864 ('864 patent) describes a self contained unit for collecting and analyzing samples of liquid specimen including a specimen container having an open capillary end and an open top with a chamber disposed there between, the chamber including a means therein for analytical testing, and, a vial having a sealed top end, the top end being of pre-selected size to receive the lower end of the sample container in a substantially air tight arrangement upon being penetrated by the capillary end. This reference is incorporated in its entirety herein. However, the self-contained unit described, has several disadvantages. Since the capillary end does not have a coating of an anticoagulant, it is a disadvantage because once the sample is drawn into the capillary end, the operator or technician has to move with speed to carry out the analysis otherwise the blood will clot in the capillary tip.

Another disadvantage of the unit described is that there is no means of filtering the sample before it is contacted with the test strip, and therefore the sample may contain contaminants and particulate matter that may interfere with the analysis of the test component.

Yet an additional disadvantage of the unit described is the lack of a support cap for the test strip at the open end of the container, thereby not allowing the inversion of the tube to allow the sample to travel along the test strip not only by absorption but also by gravity.

An additional disadvantage of the unit described in the '864 patent is that it provides no graduated means of measuring the volume of the sample collected.

The above disadvantages have been overcome in the present invention.

3. SUMMARY OF THE INVENTION

An object of the present invention is to provide a simply constructed, inexpensive, disposable non-intrusive collecting assembly or sampler for body fluids such as blood, plasma, serum, sweat, tears or saliva.

Another object of the present invention is to provide a sampler for collecting liquid specimens that utilize sample containers with open capillaries, said capillaries being of varying length or diameter, for the collection of liquid specimens for further analyses. By way of example, but not limitation, the sample container and the capillary tube may be made of materials such as glass, quartz, plastic, polypropylene, polyolefin, nylon, polyethylene terephthalate, polyethylene naphthalate polyvinyl chloride or copolymers thereof, and relatively non-reactive with the fluid samples collected.

A further object of the present invention is to provide a sampler with open capillaries, said capillaries being coated with an anticoagulant selected from the group consisting of heparin, EDTA and sodium citrate, or a detergent to cause lysis of the blood or fluid components, a stabilizer to prevent the biological marker from degrading, a preservative to facilitate the storage of the sample, or a combination thereof of one or more agents.

To these and other ends, the present invention broadly contemplates the provision of a one piece barrel assembly comprising a capillary tube having an open capillary end, and an anticoagulant of choice, a detergent, a stabilizer or a preservative coating the inner lining of the capillary end for contact with a fluid to be collected. The barrel assembly includes a filter membrane fitted above the capillary end at the junction of the first open end of the barrel assembly and the capillary tube. The barrel assembly may further include a means for analytical testing of the sample. The barrel assembly has a second open end opposed to the first end, and may optionally be provided with a support means for the test strip at the second open end. The open capillary end of the barrel assembly may be provided optionally with a first tip cap for closing the open end of the capillary tube projecting there from. The invention also provides a sealed vial containing an analytical testing reagent, the vial being substantially airtight and sealed with a pierceable material, specifically by the open capillary end.

Still another object is to provide a specimen collecting, processing and analytical assembly of such type that is easily understood and used by the person from whom the specimen is obtained and the person obtaining it (for example in home care or field situations), the assembly having a shape and size similar to a common barrel of a syringe or an oral fever thermometer.

A further object is to provide methods of using such specimen collecting, processing and analytical assemblies. In accordance with one aspect of the invention, an assembly of the type described is employed in a method of collecting, preparing and analyzing a body fluid specimen or any fluid specimen, said method comprising the steps of 1) bringing a fluid specimen to be collected into contact with the open capillary end for collection of the specimen by capillary action into the capillary tube, collecting a specific volume of the specimen using graduated volumetric markings provided optionally on the capillary tube, 3) piercing the vial containing an analytical agent with the capillary end to dilute the specimen, drawing the diluted specimen through the capillary tube, 4) filtering the diluted specimen through a filter membrane, and optionally, 5) analyzing the processed sample by immunochemical or biochemical assays.

The diluted specimen may pass outwardly from the vial into the barrel container by capillary action, propelled by pressure force from the vial or by gravity flow, that is, with the tube supported in an inverted position with the capillary tube pointing upward while the interior of the tube is filled with the diluted specimen that is filtered through a filter membrane.

In accordance with a further aspect of the invention, the assembly may be provided with an analytical element such as a strip of test paper or other material having incorporated therein an agent that undergoes an observable change, for example, a visually observable change, or a change that may be observed with an appropriate detecting instrument, upon contact with a substance to be detected in a body fluid specimen. The analysis element has a proximal end mounted in the support means, such that when the support means is in position closing the second end of the tube, the analysis element extends through the tube, and its distal end is in fluid transferring contact with the filter to receive filtered fluid coming from the vial.

In an alternate embodiment, the support means may be a disc such that when the disc is in position closing the second end of the tube, the analysis element extends through the tube, with its proximal end supported by the disc, and its distal end is in fluid transferring contact with the filter to receive filtered fluid specimen coming from the vial.

Any one of the embodiments of the present invention may include a first tip cap that sealbly fits the open end of the capillary tube, and/or a second cap that sealable fits the top open end of the barrel container, when the reagent vial is removed. It is also contemplated the various assemblies of the present invention may be used to store the specimens collected immediately after collected, or after processing the specimens, and accordingly the material used to construct the assembly will be chosen to prevent loss of sample or gas leakage through the assembly walls.

It is also contemplated to provide a packed column of analytical powder or particles, for example, conventional chromatographic material in particulate form, filling the entire interior of the tube and either in direct contact with the inner extremity of the capillary end or isolated there from by a filter, again for the purpose of enabling analysis of a sample by observation of the packed column through the tube wall.

The invention also provides special packaging kits to facilitate servicing the user, for example, for an individual having a routine health check up, a packaging kit may include a plurality of assemblies for collecting blood in heparin, EDTA, sodium citrate, buffer, and a tube for a urine specimen. Alternately, a kit may include a plurality of assemblies of any one kind.

4. BRIEF DESCRIPTION OF FIGURES

A better understanding of the present invention may be obtained from the following detailed description of the preferred embodiments described in connection with the accompanying drawings wherein.

5. DETAILED DESCRIPTION OF THE INVENTION

Figure 1:
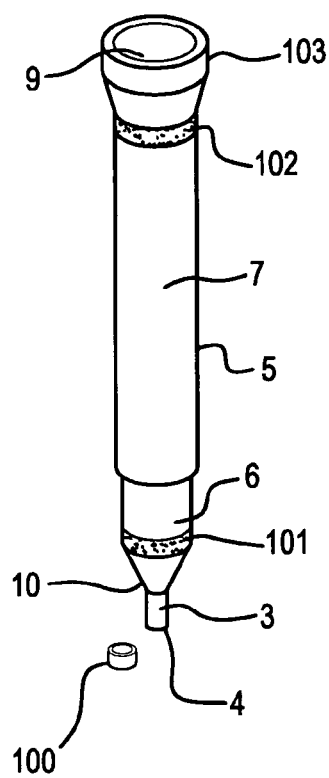
FIG. 1 is a perspective view of the sample container of the present invention.

Referring to FIG. 1, a barrel container 5 is provided with a capillary tube 3 having an open capillary end 4, and an open top 9 with a chamber 7 disposed there between. Variations in the shape of the barrel container 5, the position of the open top 9, as well as the size and shape of capillary tube 3 may exist depending upon the particular liquid specimens to be analyzed. For example, for the collection of a small volume of about 1 to 5 µl, a capillary tube 3 having a short length of about 3 to 5 mm, a narrow diameter of about 0.1 2.0 mm,with a small capillary opening 4 is advantageous. However, for the collection of larger volumes of about 6 to 100 µl of a fluid, a capillary tube 3 with a longer length 3 of about 0.5 to 20 mm, a diameter of about 1 to 5 mm, a funnel shaped opening as described in the U.S. Pat. No. 5,935,864, is preferred. The dimensions and design of the capillary tube would be adapted to hold volumes of 100 µl to 2000 µl. The capillary tube portion 3 may be volumetrically graduated to indicate different volumes from 1 to 2000 µl, the marking made with different colors to indicate the coating used to line the tube internally. The volume markings may thus be color coded purple (EDTA), green (heparin), blue (sodium citrate), red (serum), yellow (stabilizer) or black (preservative). For collecting larger volumes by the capillary tube 3, the operator may optionally speed up the drawing of fluid by capillary action by using a rubber tip at opening 9 of the barrel container to create suction, very similar to the action by which the rubber tip draws fluid into a pasteur pipette, or with customized adapters for pipette usually found in most laboratories.

The inner lining 10 of the capillary tube 3 is made of a material having properties that encourage different types of fluids such as blood and blood products, urine, sweat, tears, pericardial fluid, peritoneal fluid, pleural fluid, cerebrospinal fluid, gastric fluid, respiratory secretions, semen, synovial fluid, vomitus, wound and ulcer drainage, ascites, amniotic fluid or saliva, to be drawn by capillary action and rise into the capillary tube 3 in a pre-defined volume. For blood, the inner lining 10 of the capillary tube 3 may be coated with a sufficient amount of an anticoagulant for samples in which the measurements of the components have to be carried out in plasma.

The coagulant used may be selected from the group consisting of EDTA, heparin, and sodium citrate.

For samples that require lysis of the blood components the inner lining 10 of the capillary 3 may be coated with a detergent.

For samples requiring storage for varying times, the inner lining 10 of the capillary may be coated with a preservative or a stabilizer to prevent the components of interest from degrading. The stabilizing agent is able to stabilize nucleic acids in biological fluids at the point of collection to prevent enzymatic degradation of the nucleic acids and include cationic compounds, detergents, chaotropic salts, ribonuclease inhibitors, chelating agent, and mixtures thereof.

Preservative include, but are not limited to, antibiotics, sodium azide or antifungal agents. The inner lining 10 of the capillary tube 3 may be lined with one or more combinations of any of the above agents.

A first tip cap 100 having a suitable design, size that sealably fits the tip 4 of the capillary, may be included in the kit to be used when the sample is not analyzed promptly after the collection step.

The barrel container 5 comprises of the tip 4 of the capillary tube 3 at the bottom end, a short and narrow barrel portion 6 and a chamber 7. At one end of the shorter narrower barrel portion 6, is placed a filter membrane 101 that fits over one of the end of the capillary 3. One end of the chamber 7 is in contact with the end of the narrower barrel portion 6 forming a ridge 106. At the second end of the chamber portion 7, is placed a support means 102 to fit a rim 103 at the top end of the barrel container 5. The filter membrane 101 is made of a variety of materials that are non-reactive and serve filtering functions. The support means 102 is in the shape of a disc having the diameter of the same size as the inner diameter of the barrel container, and is made of non-reactive materials and serves supporting functions. The fitting of the support means 102 is not airtight and allows air flow through the barrel container.5

Figure 2:
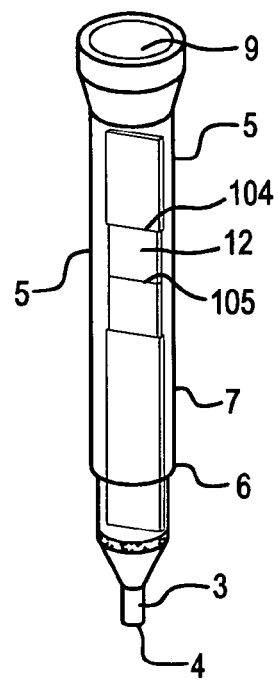
FIG. 2 is a perspective view of the sample container of FIG. 1 with a filter inserted above the capillary tube, a test strip inserted above the filter, and a support means inserted above the test strip.

Referring to FIG. 1 and FIG. 2, the chamber 7 houses a test strip 12 for analysis of the test component in the body fluid to be analyzed. These test strips are well known in the prior art and described in detail in scientific literature. A valid test performance is indicated by a colored line 104, and presence of antibodies against an antigen is also indicated by a second colored line 105.

The analytical methods may be immunochemical or non-immunochemical techniques for analytes that may be detected using inorganic chemical reactions.

Figure 3:
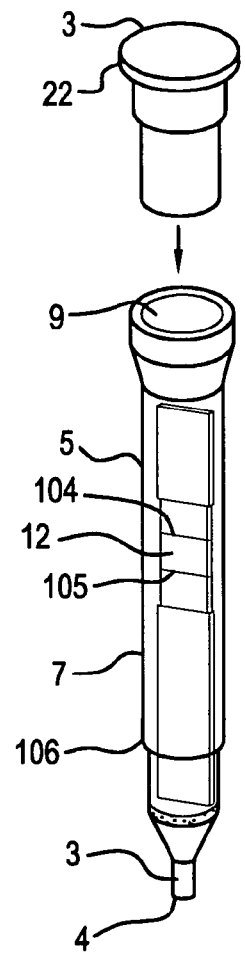
FIG. 3 is a perspective view of the sample container of FIG. 2 with a vial having a sealed top placed and a size to receive the lower end of the sample container in an airtight arrangement.

Referring to FIG. 3, a vial 20 having a sealed top 22 is fitted into an airtight arrangement with the rim 103 at the top end of the sample container 5.

Figure 4:
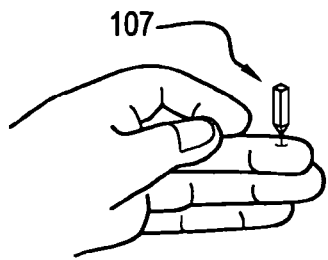
FIG. 4 is a perspective view of a lancet being applied to prick a finger.

FIG. 4 shows a lancet 107 being applied to prick a finger, ear, toe, or heel, to draw blood. The specimen may be contained in a tube (for example a serum or plasma sample) or be in situ in the body, for example, saliva in the mouth, or drawn by a physician or nurse, for example, pericardial fluid, peritoneal fluid, pleural fluid, cerebrospinal fluid, gastric fluid, respiratory secretions, semen, synovial fluid, wound and ulcer drainage, ascites, or amniotic fluid.

Figure 5:
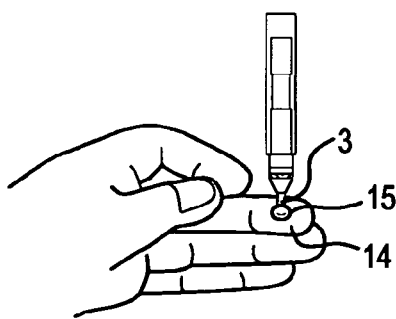
FIG. 5 is a perspective view of the sample container of FIG. 2 shown in contact with a liquid specimen source.
Figure 6:
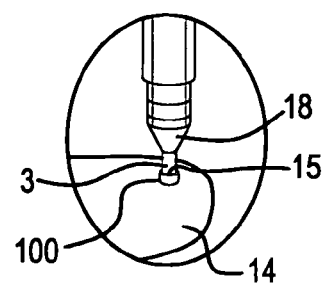
FIG. 6 is a perspective view of the sample container of FIG. 5 with the open capillary end sealed with a cap.

FIG. 5 shows the technique of contacting the open capillary end 4 to the drop of blood or liquid specimen 15, to draw the blood up the capillary tube 3 by capillary action. The liquid specimen to be analyzed is shown as a drop of blood 15 that is obtained by pricking a finger 14 with a medical lancet, or a sharp object, for example, a sharpened end of the capillary open end 4. The dimensions and material of the capillary tube 3 and the surface tension of the liquid determine the extension of the upper meniscus 18 in the capillary as shown in FIG. 6 and the volume of the liquid picked up. The capillary tube may be titlted sideways to facilitate drawing of the liquid by capillary action, or optionally, the operator may use a Pasteur pipette rubber tip of a pipette adaptor at the open end 9 to aid the drawing of volumes in the range of 100 µl to 2000 µl. Optionally, the capillary tube 3 may be graduated with color markings to indicate different volumes, for example, 1 to 2000 µl or more. The graduated volumetric markings may be in colors corresponding to the conventional colors of anticoagulants, for example, heparin in green for a capillary end coated with heparin, purple for EDTA, blue for sodium citrate, red for serum, and yellow for a stabilizer, black for a preservative or other color schemes for different types of products.

FIG. 6 shows an embodiment of the barrel container 5 having the capillary end 4 sealably capped by a tip cap 100 to prevent the sample from leaking when the operator is unable to process and analyze the sample promptly, or in instances when the operator is collecting samples and storing them to be analyzed at a later time. In this situation, after collecting the sample, the assembly is shaken gently to mix the sample with the coating agent inside the capillary tube, and stored in a suitable rack in vertical or horizontal position.

Figure 7:
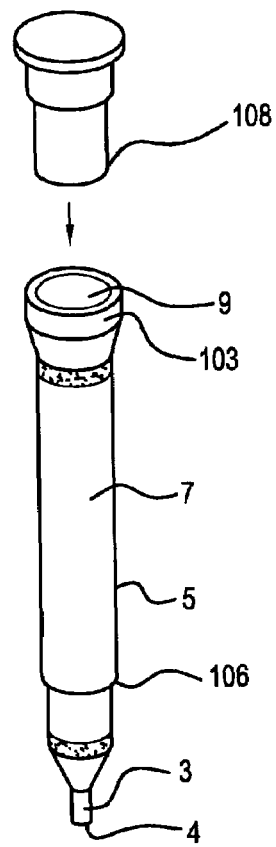
FIG. 7 is a perspective view of the sample container of FIG. 2 with the support means consisting of a further cap.

FIG. 7 describes an embodiment of the barrel container 5 in which the top end has fitted tightly on the rim 103, a second cap 108 to seal the top end 9. The shape and size of the second cap 108 may be designed in different forms, or color coded similar to the graduations on the capillary tube 3, depending on the fluid being measured and the test being carried out. This is because measurements of different factors are expressed per unit of plasma, serum or liquid. This embodiment may optionally include the analytical device as described in FIG. 2. However, the embodiment may be used only as a collecting device for small amounts of fluid (10 to 1000 µl). The unit may be capped with the first tip cap 100 and the second cap 108, stored in a suitable carrying tray and shipped to a clinical laboratory for analysis. The caps 100 and 108 may be color coded similar to the volumetric graduations 110 on the length of the capillary tube 3, for example purple for EDTA, green for heparin, blue for sodium citrate, red for serum, yellow for stabilizer and black for preservative.

In another embodiment, the sample may be collected through the capillary end 4 that pierces through a solvent vial 20 to dilute the sample. The sample barrel container 5 is then inverted, sample shaken gently and the diluted sample is allowed to pass through the filter 101 and collect in the chamber 7 which has its top end 9 sealbly closed with the second cap 108. The sample container is stored in a rack with the vial still fitted at the capillary end, or with the vial removed and capillary end capped with the first tip cap 100.

Figure 8:
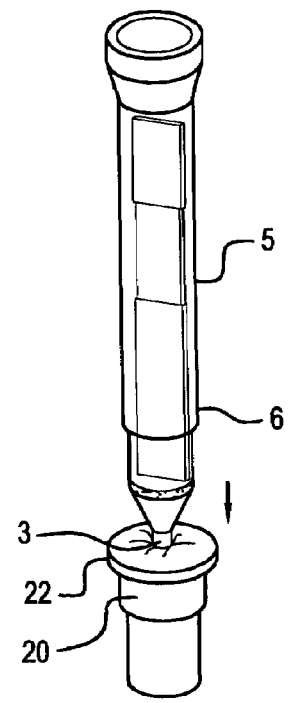
FIG. 8 is a perspective view of the sample container and reagent vial of FIG. 5 with the capillary end of the sample container being inserted into the reagent vial.
Figure 9:
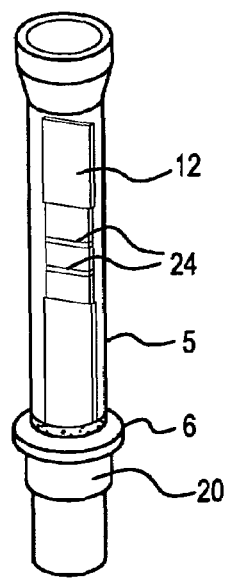
FIG. 9 is a perspective view of the sample container of FIG. 8 with the capillary end inserted into the reagent vial and the diluted sample in contact with the test strip.

FIG. 8 shows the capillary end 4 being forced through the septum 22 and subsequently into a solvent vial 20. The solvent may be an aqueous of non-aqueous medium, for example, a buffer solution, saline, water or other solvent and is packed under a vacuum. The liquid in the capillary tube 3 is diluted and flushed into the chamber 7 of the barrel container 5. The sample container 5 is provided with an inwardly extending portion 6 engageable with an opening in the penetrable foil and that fits airtight into the vial 20 thus inducing a pressure that flushes the content of the vial 20 through the capillary tube 3. The resulting liquid/buffer mixture enters the chamber 7 where it is analyzed. The barrel container 5 is also provided with a filter 101 through which the liquid gets filtered and comes into contact with the proximal end of a test strip and travels up the strip. For example, in using immuno-chromatographic test strip 12 for analyzing the liquid buffer mixture as indicated by lines 24 in FIG. 9 an indication as a control and reaction indicator can be generated as those described in U.S. Pat. Nos. 4,299,916; 4,235,601; and 5,141,850. The proximal end of the test strip is in contact and supported by a support means 102. As the liquid travels along the strip the sample container 5 may be inverted to make the flow faster by gravity.

Figure 10:
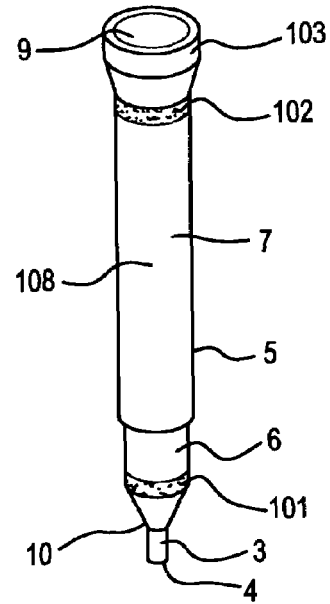
FIG. 10 is a perspective view of a sample container with a chromatographic material inserted in the barrel portion instead of a test strip.

FIG. 10 describes yet another embodiment of the invention, a sampling and analytical device in which the immuno-chromatographic separation is done using a suiting column and packing material 108.

FIG. 11 represents one of many possible examples of packaging suitable for the device of the invention, in lots of varying numbers, for example, 5, 10, 20, 50, 100, etc, one single plastic trays or stacked trays to provide convenient color coded kits that hold collection devices requiring different anticoagulants, stabilizers, detergents or preservatives. Such a tray unit could be used for collecting, shipping and storage of samples procured per patient thereby reducing the risk of losing or mistakenly mixing patient samples.

Thus, a cost effective, portable, easily operable collection and analytical device and its different embodiments is described.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims. It is realized that other variations and modifications of the preferred embodiment are possible without departing from the scope and spirit of the present invention. Those skilled in the art will recognize, or be able to ascertain using no more than routine experimentation, any equivalents to the embodiments described herein. Such equivalents are intended to be encompassed by the claims.

What is claimed is:

1. A specimen collecting and analytical assembly comprising in combination:
   a. a one piece barrel container having an open top and a capillary tube with an open end, with a chamber disposed there between,
   b. the chamber having a support means at the distal end and a single disc-shaped filter membrane placed at the proximal end of the chamber, so that the chamber portion below the filter membrane is narrowed to a smaller diameter and extended in the shape of a capillary tube,
   c. said capillary tube being designed to draw a sample up to 2000 µl,
   d. said capillary tube being volumetrically graduated externally with specific color markings, and internally coated with an agent including a buffer, anticoagulant, detergent, stabilizer or a preservative, and
   e. wherein the top of the barrel houses a vial containing a suitable reagent packed under vacuum therein.

2. The specimen collecting and analytical assembly of claim 1 further comprising an analytical means housed between the support means and the filter membrane.

3. The specimen collecting and analytical assembly of claim 1, wherein the barrel container is made of a material selected from the group consisting glass, quartz, plastic, polypropylene, polyolefin, nylon, polyethylene terephthalate, polyethylene naphthalate polyvinyl chloride or copolymers thereof.

4. The specimen collecting and analytical assembly of claim 1 wherein said capillary tube comprises a diameter of about 0.1 to 5.0 mm, a length of about 5.0 to about 20 mm, and an interior volume of about 1 to about 2000 µl.

5. The specimen collecting and analytical assembly of claim 1 further comprising a tip cap sealable fitted to the open capillary end.

6. The specimen collecting and analytical assembly of claim 1, further comprising a second cap sealably fitted to close the top end of the barrel container.

7. The specimen collecting and analytical assembly of claim 1 wherein said vial has a penetrable foil seal.

8. The specimen collecting and analytical assembly of claim 7 wherein said barrel container includes means to form an air tight seal and said penetrable foil upon receipt of said capillary tube.

9. The specimen collecting and analytical assembly of claim 8, wherein said barrel container has an inwardly extending portion, said inwardly extending portion engageable with an opening in said penetrable foil to form an airtight seal between said barrel container and said vial.

10. The specimen collecting and analytical assembly of claim 2, wherein said support means defines the location of one end of the analytical means housed in the chamber.

11. The plurality of specimen collecting and analytical assemblies according to claim 1, housed in a packaging tray, wherein the assemblies comprise color coded graduated volumetric capillary tubes, color coded tip caps and color coded second caps, all corresponding to the coating applied internally in the capillary tube, including green for heparin, purple for EDTA, blue for sodium citrate, red for serum, yellow for stabilizer and black for preservative.

* * * * *